United States Patent [19]

Tong et al.

[11] 4,202,967
[45] May 13, 1980

[54] N,N-PENTAMETHYLENE DERIVATIVES OF DAUNOMYCIN AND ADRIAMYCIN

[75] Inventors: George L. Tong, Cupertino, Calif.; David W. Henry, Chapel Hill, N.C.; Helen Y. Wu, San Jose; Thomas H. Smith, San Carlos, both of Calif.

[73] Assignee: SRI International, Menlo Park, Calif.

[21] Appl. No.: 947,463

[22] Filed: Oct. 2, 1978

[51] Int. Cl.² .................................. C07H 15/24
[52] U.S. Cl. ................................ 536/17 A; 424/180
[58] Field of Search ....................... 536/17 A, 17

[56] References Cited

U.S. PATENT DOCUMENTS 4,039,736  8/1977  Nettleton et al. ................. 536/17 A

FOREIGN PATENT DOCUMENTS 5119701  8/1974  Japan ..................... 536/17 A

OTHER PUBLICATIONS

Henry et al., "Abstract of Papers 172nd ACS Meeting, Amer. Chem. Soc.", San Francisco, Calif. 8/29–9/3/76, Port City Press, Inc., Baltimore, Md., #90.
Zbinden, "Toxicology Letters", No. 1, 1978, pp. 267–274, Elsevier North–Holland Biomedical Press.

Primary Examiner—Johnnie R. Brown
Attorney, Agent, or Firm—Donovan J. De Witt

[57] ABSTRACT

Described are N,N-pentamethylene derivatives of daunomycin and adriamycin having the formula:

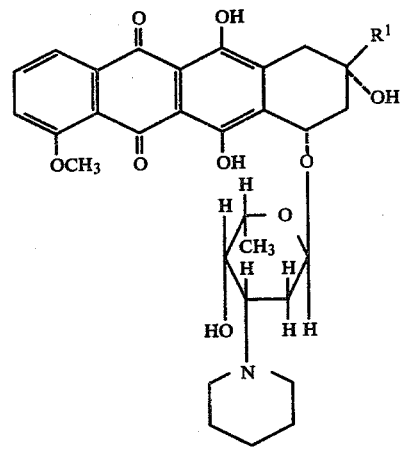

wherein $R^1$ is —COCH$_3$ or —CHOHCH$_3$ in the case of daunomycin derivatives, or —COCH$_2$OH or —CHOHCH$_2$OH in the case of adriamycin derivatives. The compounds have utility as antitumor agents.

5 Claims, No Drawings

N,N-PENTAMETHYLENE DERIVATIVES OF DAUNOMYCIN AND ADRIAMYCIN

ORIGIN OF INVENTION

The invention described herein was made in the course of or under a contract with the Department of Health, Education and Welfare.

BACKGROUND OF THE PRIOR ART

Adriamycin and daunomycin derivatives wherein the amino hydrogens in the sugar moiety are replaced by methyl groups to provide a N,N-dimethyl tertiary amine moiety are described in the following references:

1. G. Zbinden, M. Pfister and CH. Holderegger, Cardiotoxicity of N,N-Dimethyladriamycin (NSC-261 045) in Rats, Toxicology Letters, 1(1978), pp 267–274, and
2. David W. henry, George Tong, Allan N. Fujiwara, William W. Lee, Methylated Analogs of Daunomycin and Adriamycin, American Chemical Society, Abstract of Papers, 172nd ACS Meeting, San Francisco, California, Aug. 29–Sept. 3, 1976.

The compounds of the present invention differ from those of the prior art in that they do not represent alkyl amine derivatives of adriamycin and daunomycin. Instead, they are adiramycin or daunomycin derivatives wherein the amino nitrogen atom of the sugar moiety forms a part of a piperidino ring which resembles, in some measure, a second sugar ring in the molecule.

SUMMARY OF INVENTION

The present invention relates to the provision of novel daunomycin and adriamycin derivatives having the formula

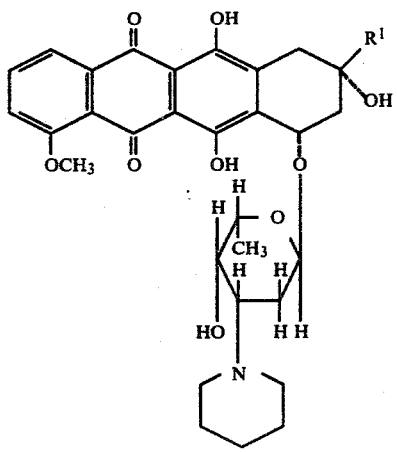

wherein $R^1$ is —$COCH_3$ or —$CHOHCH_3$ in the case of daunomycin derivatives, or —$COCH_2OH$ or —$CHOHCH_2OH$ in the case of adriamycin derivatives. Specifically, the invention covers the four compounds of Examples I and II, together with their acid addition salts. Such salts are water soluble and are therefore of somewhat greater utility than the compounds would be without inclusion of the acid component. In preparing the compounds as salts, any pharmaceutically acceptable acid material may be employed, e.g., hydrochloric acid, sulfuric acid, citric acid, or acetic acid, for example.

Compounds of the present invention have utility as antitumor agents. Tested in vitro they are effective inhibitors of nucleic acid synthesis.

The following examples describe the method of preparation of each of the compounds of the present invention:

EXAMPLE 1

N,N-Pentamethylenedaunorubicin (1) and N,N-Pentamethylene-13-dihydrodaunorubicin (2)

Glutaraldehyde (0.12 ml of 25% aqueous solution, 0.3 mmol) was added to daunorubicin hydrochloride (169 mg, 0.3 mmol) in 3:1 acetonitrile-water (4 mL) and the solution stirred at 23° for 30 minutes. Sodium cynoborohydride (19 mg, 0.3 mmol) was added and the mixture was stirred at 23° for 4 hours. The reaction mixture was diluted with saturated NaCl and extracted with $CHCl_3$ (4×10 ml). The extracts were combined, washed with water (5 mL), dried and evaporated. The residue was chromatographed (prep layer chromatography, silica gel 60 2 plates 40:10:1 $CHCl_3.MeOH.H_2O$) to afford 54 mg (30%) of 1: TLC (40:10:1 $CHCl_3$ MeOH $H_2O$) $R_f$ 0.58; [α] +255° (EtOH) c 0.05 and 20 mg (11%) of 2: TLC (40:10:1 $CHCl_3.MeOH.H_2O$) $R_f$. 40. These materials were converted to the HCl salts via treatment with a molar equivalent of methanolic HCl followed by precipitation with ether.

EXAMPLE 2

N,N-Pentamethyleneadriamycin (3) and N,N-Pentamethylene-13-dihydroadriamycin (4)

Glutaraldehyde (4.8 mL of 25% aqueous solution, 6.0 mmol) was added to adriamycin hydrochloride (3.48 g, 6.0 mmol) in 30:13 acetonitrile-water (215 ml) and stirred at 23° for 30 minutes. The solution was added dropwise over 30 minutes to a stirred solution of $NaCNBH_3$ (377 mg, 6.0 mmol) in 3:1 acetonitrile-water (80 mL). The solution was stirred at 23° for two hours, diluted with $H_2O$ (150 mL), saturated with NaCl, and extracted with $CHCl_3$ (4×300 mL). The residue was chromatographed (dry column and prep layer silica gel chromatography 40:10:1 $CHCl_2.MeOH.H_2O$) to afford 560 mg (15%) of 3: TLC (40:10:1 $CHCl_3$ MeOH $H_2O$) $R_f$ 0.5 and 850 mg (23%) of 4: TLC (40:10:1 $CHCl_3.MeOH.H_2O$) $R_f$ 0.3. The materials were converted to their HCl salts as described above.

| | | Elemental Analyses | | | | | |
|---|---|---|---|---|---|---|---|
| | | C | | H | | N | |
| Cpd | Formula | Calcd | Found | Calcd | Found | Calcd | Found |
| 1 | $C_{32}H_{37}NO_{10} \cdot 2H_2O$ | 60.84 | 61.09 | 6.54 | 6.23 | 2.22 | 2.43 |
| 2 | $C_{32}H_{39}NO_{10} \cdot 1.75H_2O$ | 61.09 | 61.19 | 6.81 | 6.51 | 2.23 | 2.25 |
| 3 | $C_{32}H_{37}NO_{11} \cdot HCl \cdot 1.5H_2O$ | 56.93 | 57.14 | 6.12 | 6.33 | 2.07 | 2.13 |
| 4 | $C_{32}H_{39}NO_{11} \cdot HCl \cdot 0.5H_2O$ | 58.31 | 58.33 | 6.27 | 6.12 | 2.13 | 2.24 |

As indicated above, the compounds of the present invention have improved antitumor activity. This is evidenced by the data given below. In one operation, conducted in accordance with Protocol 1200 set forth in Cancer Chemotherapy Reports, National Cancer Institute, Vol. 3, No. 2, Part 3, September 1972, healthy mice were inoculated i.p. with Limphocytic Leukemia P-388 ascitic fluid. The inoculated mice were then treated i.p. for the succeeding 9 day period with varying amounts of the test chemicals of Example 2 while others of the mice were similarly inoculated with adrimycin hydrochloride and with daunomycin hydrochloride, the dosage pattern being set forth in the table given below. The average survival times of the treated mice was then determined, as was that of the control mice, which were inoculated with the ascitic fluid but given no treatment with the test chemicals. Presented in the following table under the T/C column headings are data obtained by dividing the survival time of the treated mice with that of the control mice, the quotient so obtained being multiplied by 100.

Also presented in the table are the results of in vitro tests using cultured L1210 cells in which the activity of each chemical enumerated in the following table is presented in relation to its potency as an inhibitor of nucleic acid synthesis. Data for daunomycin and adriamycin are also included in the table for the sake of comparison. More specifically, the inhibition of the synthesis of DNA and RNA by each compound was measured as a function of its activity in inhibiting incorporation of tritiated $^3$H-thymidine or $^3$H-uridine into DNA and RNA, respectively. $ED_{50}$ represents the concentration, in micromolar units, which inhibits incorporation of 50% of tritiated $^3$H-thymidine or $^3$H-uridine into the DNA and RNA of the test cells.

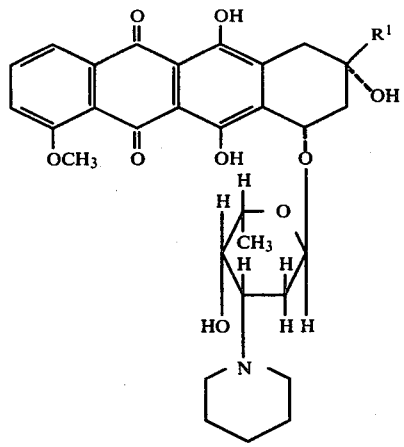

wherein $R^1$ is selected from the group consisting of —COCH$_3$, —CHOHCH$_3$, —COCH$_2$OH and —CHOHCH$_2$OH and the pharmaceutically acceptable acid addition salts of said compounds.

2. The compound of claim 1 which is N,N-pentamethylene-daunorubicin and its pharmaceutically acceptable acid addition salts.

3. The compound of claim 1 which is N,N-pentamethylene-13-dihydrodaunorubicin and its pharmaceutically acceptable acid addition salts.

4. The compound of claim 1 which is N,N-pentamethyleneadriamycin and its pharmaceutically acceptable acid addition salts.

5. The compound of claim 1 which is N,N-pentamethylene-13-dihydroadriamycin and its pharmaceutically acceptable acid addition salts.

| COMPARISON OF BIOLOGICAL DATA FOR DAUNORUBICIN, ADRIAMYCIN, AND N-ALKYL ANALOGS | | | | | | | | |
|---|---|---|---|---|---|---|---|---|
| | | Nucleic Acid Syn Inhibn,[a] | | | Antitumor Activity in Mice[b] | | | |
| | | | | | (P388, qd 1-9) | | (P388, qd 5,9,13) | |
| | | $ED_{50}$ µM | | DNA | Opt. Dose, | | Opt. Dose, | |
| Compound | $\Delta Tm$,[a] °C. | DNA | RNA | RNA | (mg/kg) | T/C[c] | (mg/kg) | T/C |
| Daunomycin hydrochloride | 11.2 | 0.66 | 0.33 | 2.0 | 0.78 | 160 | 8 | 132 |
| Adriamycin hydrochloride | 13.4 | 1.5 | 0.58 | 2.6 | 0.78 | 197 | 8 | 159 |
| N,N-Pentamethyleneadriamycin hydrochloride | 15.4 | 0.70 | 0.04 | 17.5 | 3.13 | 190 | 9.4 | 155 |
| N,N-Pentamethylene-13-dihydro-adriamycin hydrochloride | 12.5 | 0.72 | 0.10 | 7.2 | 1.56 | 157 | 18 | 143 |

[a]$\Delta Tm$ and $Ed_{50}$ values were determined by the method of G. Tong, W. W. Lee, D. R. Black, and D. W. Henry, J. Med. Chem., 19, 395 (1976), except that the drugs were initially dissolved in a volume of DMSO that resulted in a final DMSO concentration of 5 and 1%, respectively, in the assay medium. This modification greatly aided solubilization and did not affect assay results, according to extensive control experiments.
[b]Assays arranged through Drug Research and Development Program, Division of Cancer Treatment, National Cancer Institute. BDF or CDF mice are injected ip with 10⁶ P388 lymphocytic leukemia cells on Day 0 and are treated ip on Days 1-9 or days 5, 9, 13 with the specified drug dose. For detailed protocols see R. I. Geran, N. H. Greenberg, M. M. MacDonald, A. M. Schumacher, and B. J. Abbott, Cancer Chemother. Rep., Part 3, 3, (2), 9 (1972).
[c]Ratio of average survival times of treated mice to untreated controls in percent. The average survival time of untreated controls is approximately 11 days. Activity is defined as values of T/C ≧ 120 in the qd 5, 9, 13 protocol and T/C ≧ 125 in the qd 1-9 protocol.

What we claim is:
1. Compounds of the formula